(12) United States Patent
Sukeda et al.

(10) Patent No.: US 11,942,228 B2
(45) Date of Patent: Mar. 26, 2024

(54) DEVICE FOR PREDICTION OF REACTOR WATER QUALITY OF NUCLEAR REACTOR

(71) Applicant: Hitachi-GE Nuclear Energy, Ltd., Ibaraki (JP)

(72) Inventors: Hiroko Sukeda, Tokyo (JP); Naoshi Usui, Hitachi (JP); Mayu Sasaki, Hitachi (JP); Hideyuki Hosokawa, Tokyo (JP); Tsuyoshi Ito, Tokyo (JP)

(73) Assignee: HITACHI-GE NUCLEAR ENERGY, LTD., Hitachi (JP)

( * ) Notice: Subject to any disclaimer, the term of this patent is extended or adjusted under 35 U.S.C. 154(b) by 258 days.

(21) Appl. No.: 17/082,057

(22) Filed: Oct. 28, 2020

(65) Prior Publication Data

US 2021/0210231 A1    Jul. 8, 2021

(30) Foreign Application Priority Data

Nov. 22, 2019   (JP) ................................. 2019-211549

(51) Int. Cl.
*G21C 17/022*    (2006.01)
*G01N 33/18*     (2006.01)
*G21D 3/00*      (2006.01)

(52) U.S. Cl.
CPC ............ *G21C 17/022* (2013.01); *G01N 33/18* (2013.01); *G21D 3/001* (2013.01)

(58) Field of Classification Search
CPC ....... G21C 17/022; G01N 33/18; G21D 3/001
(Continued)

(56) References Cited

U.S. PATENT DOCUMENTS

2021/0074442 A1* 3/2021 Hoover .................. G21D 3/002
2021/0098142 A1* 4/2021 Hosokawa ............. G21C 17/10

FOREIGN PATENT DOCUMENTS

| JP | 4-84799 A    | 3/1992 |
| JP | 06-289179 A  | 10/1994 |
| JP | 2000-028726 A | 1/2000 |

OTHER PUBLICATIONS

Song, "A Study on the Application of Crudtran Code in Primary Systems of Domestic Pressurized Heavy-Water Reactors for Prediction of Radiation Source Term", Nuclear Engineering and Technology 49, No. 3 (2017): 638-644. (Year: 2017).*

(Continued)

*Primary Examiner* — Jack W Keith
*Assistant Examiner* — Daniel Wasil
(74) *Attorney, Agent, or Firm* — MATTINGLY & MALUR, PC

(57) ABSTRACT

More accurate prediction of reactor water quality of a nuclear reactor is implemented. A device for prediction of reactor water quality of a nuclear reactor in a nuclear power plant is disclosed. The device stores a reactor water quality prediction model which is learned using learning data, and with which future reactor water quality is predicted. An explanatory variable of the reactor water quality prediction model includes a value in a predetermined period unit that is generated from data acquired in an operating nuclear power plant. The device generates the value in a predetermined period unit from data acquired in a target operating nuclear power plant, and acquires a predicted value of the reactor water quality in the target nuclear power plant based on the reactor water quality prediction model and the value in a predetermined period unit.

10 Claims, 12 Drawing Sheets

(58) Field of Classification Search
USPC .................................................. 376/259, 305
See application file for complete search history.

(56) References Cited

OTHER PUBLICATIONS

Cho, "A Study on the Application of Crudtran Code in Primary Systems of PWR & PHWR in Domestic NPPs for the Prediction of Radiation Source Term" (2017). (Year: 2017).*
Japanese Office Action received in corresponding Japanese Application No. 2019-211549 dated Feb. 21, 2023.

* cited by examiner

| | | | 333 PLANT-FIXED VALUE | 311 ELECTRIC OUTPUT | | 312 OPERATION DATA AND MEASURED VALUE | 313 IN-REACTOR METAL IMPURITY ACCUMULATION AMOUNT | | 314 SUPPLIED WATER QUALITY DATA | | | | 315 REACTOR WATER QUALITY | | | | | 316 |
|---|---|---|---|---|---|---|---|---|---|---|---|---|---|---|---|---|---|
| 331 PLANT | 332 DATE | CYCLE NUMBER | REACTOR TYPE ... | DAILY ELECTRIC OUTPUT | CYCLE ACCUMU-LATION | A PUMP PRESSURE DIFFERENCE ... | IRON ACCUMU-LATION AMOUNT | COBALT ACCUMU-LATION AMOUNT | IRON IN SUPPLIED WATER | COBALT IN SUPPLIED WATER ... | DISSOLVED OXYGEN IN SUPPLIED WATER | ELECTRIC CONDUC-TIVITY OF SUPPLIED WATER | COBALT-60 ... | COBALT-58 | IRON IN REACTOR WATER | COBALT IN REACTOR WATER ... | DISSOLVED OXYGEN IN REACTOR WATER | ELECTRIC CONDUC-TIVITY OF REACTOR WATER ... |
| PLANT A | 2001/9/13 | 3 | | | | | | | | | | | | | | | | |
| PLANT A | 2001/9/14 | 3 | | | | | | | | | | | | | | | | |
| PLANT A | 2001/9/15 | 3 | | | | | | | | | | | | | | | | |
| PLANT A | 2001/9/16 | 3 | | | | | | | | | | | | | | | | |
| PLANT A | 2001/9/17 | 3 | | | | | | | | | | | | | | | | |
| PLANT A | 2001/9/18 | 3 | | | | | | | | | | | | | | | | |
| PLANT A | 2001/9/19 | 3 | | | | | | | | | | | | | | | | |
| ... | | | | | | | | | | | | | | | | | | |
| PLANT B | 2006/7/1 | 6 | | | | | | | | | | | | | | | | |
| PLANT B | 2006/7/2 | 6 | | | | | | | | | | | | | | | | |
| PLANT B | 2006/7/3 | 6 | | | | | | | | | | | | | | | | |
| PLANT B | 2006/7/4 | 6 | | | | | | | | | | | | | | | | |
| PLANT B | 2006/7/5 | 6 | | | | | | | | | | | | | | | | |
| PLANT B | 2006/7/6 | 6 | | | | | | | | | | | | | | | | |
| PLANT B | 2006/7/7 | 6 | | | | | | | | | | | | | | | | |
| ... | | | | | | | | | | | | | | | | | | |

PLANT INFORMATION DB

| PLANT | DATE | CYCLE NUMBER | COBALT-60 CONCENTRATION IN REACTOR WATER AFTER 30 DAYS |
|---|---|---|---|
| PLANT A | 2001/9/13 | 3 | 2.2 |
| PLANT A | 2001/9/14 | 3 | 2.3 |
| PLANT A | 2001/9/15 | 3 | 2.35 |
| PLANT A | 2001/9/16 | 3 | 2.5 |
| PLANT A | 2001/9/17 | 3 | 2.4 |
| PLANT A | 2001/9/18 | 3 | 2.4 |
| PLANT A | 2001/9/19 | 3 | 2.5 |
| PLANT A | 2001/9/20 | 3 | 2.55 |
| ... | ... | ... | |
| PLANT B | 2006/7/1 | 6 | 7.17 |
| PLANT B | 2006/7/2 | 6 | 9.66 |
| ... | ... | ... | |

OBJECTIVE VARIABLE TABLE

FIG. 8B

| | | | PLANT-FIXED VALUE | ELECTRIC OUTPUT | | OPERATION DATA AND MEASURED VALUE | | IN-REACTOR METAL IMPURITY ACCUMULATION AMOUNT | | | SUPPLIED WATER QUALITY | | | | |
|---|---|---|---|---|---|---|---|---|---|---|---|---|---|---|---|
| PLANT | DATE | CYCLE NUMBER | REACTOR TYPE | ... | DAILY ELECTRIC OUTPUT | CYCLE ACCUMU-LATION | A PUMP PRESSURE DIFFERENCE | ... | IRON ACCUMU-LATION AMOUNT | COBALT ACCUMU-LATION AMOUNT | ... | IRON IN SUPPLIED WATER | COBALT IN SUPPLIED WATER | ... | DISSOLVED OXYGEN IN SUPPLIED WATER | ELECTRIC CONDUCTIVITY OF SUPPLIED WATER |
| PLANT A | 2001/9/13 | 3 | | | | | | | | | | | | | | |
| PLANT A | 2001/9/14 | 3 | | | | | | | | | | | | | | |
| PLANT A | 2001/9/15 | 3 | | | | | | | | | | | | | | |
| PLANT A | 2001/9/16 | 3 | | | | | | | | | | | | | | |
| PLANT A | 2001/9/17 | 3 | | | | | | | | | | | | | | |
| PLANT A | 2001/9/18 | 3 | | | | | | | | | | | | | | |
| PLANT A | 2001/9/19 | 3 | | | | | | | | | | | | | | |
| ... | ... | ... | | | | | | | | | | | | | | |
| PLANT B | 2006/7/1 | 6 | | | | | | | | | | | | | | |
| PLANT B | 2006/7/2 | 6 | | | | | | | | | | | | | | |
| ... | ... | ... | | | | | | | | | | | | | | |

EXPLANATORY VARIABLE TABLE

DEVICE FOR PREDICTION OF REACTOR WATER QUALITY OF NUCLEAR REACTOR

CLAIM OF PRIORITY

The present application claims priority from Japanese patent application JP 2019-211549 filed on Nov. 22, 2019, the content of which is hereby incorporated by reference into this application.

BACKGROUND OF THE INVENTION

1. Field of the Invention

The present invention relates to a device for prediction of reactor water quality of a nuclear reactor.

2. Description of the Related Art

In a boiling water nuclear power plant, water quality control for ensuring safety and reliability is an important issue. In particular, various water quality control countermeasures are being taken with aims of reducing a dose rate of plants and ensuring soundness of fuel and equipment. A main reason of a plant dose is that incrustation (clad) generated from piping and equipment of a cooling water system and a surface of a fuel assembly is an object (radioactive corrosion products) that is activated by neutron irradiation in a reactor core. Since concentrations of cobalt-60 and cobalt-58 in reactor water, which are main components of the radioactive corrosion products, has the greatest effect on exposure of workers, by monitoring and predicting values of the concentrations, the values are used for planning periodic inspection work and implementing reduction countermeasures.

Generally, in a nuclear power plant, an operation of a plant is stopped regularly (approximately once for every one to two years) to perform a large-scale inspection. An operation period from a stop period to a stop period is referred to as an "operation cycle". Through the operation cycle, there is a trend that the chemical reactions described above increase the radioactive corrosion products in the reactor, and by removing a spent fuel during the periodic inspection work when the operation is stopped, the radioactive corrosion products are temporarily reduced. Therefore, since the radioactive corrosion products are most increased immediately after the operation is stopped (at an end of the operation cycle), water quality control in the reactor is an important issue to minimize the radiation exposure of workers during the periodic inspection work.

Regarding the water quality in the reactor, there are models that describe a behavior of the radioactive corrosion products. A representative example describes, according to a macro mass conservation law (mass balance model), dynamic behaviors of allowing a corrosion product contained in supplied water and a corrosion product generated due to corrosion of structural materials inside and outside the reactor in contact with the reactor water to be re-adhered to surfaces of fuel rods or surfaces of the structural materials inside and outside the reactor via the reactor water, and removing the corrosion products out of the system by a nuclear reactor cleanup system.

Japanese Patent Application No. 94-289179 discloses a self-learning diagnosis and prediction method and a device of a plant for executing simulations while optimizing parameters from water quality data obtained by actual measurement according to this mass balance model, and executing abnormality diagnosis and prediction. Accordingly, by improving a parameter of a simulation model based on measurement data of an actual plant, water quality in the plant can be diagnosed and predicted.

JP-A-2000-28726 discloses a method of obtaining a predicted value of a work dose and a dose transition curve at the time of periodic inspection by giving a cobalt-60 concentration in the reactor water and the like as an input in a situation where the cobalt-60 concentration and the like is obtained. Accordingly, by creating a multiple regression equation using water quality analysis data, environmental dose rate data, construction record data, and the like, a dose rate at the time of a next periodic inspection can be obtained, which can be useful for planning the periodic inspection work.

For example, in the reactor water quality control in the related art, since a main aim is to reduce the exposure during the periodic inspections, the prediction of the reactor water quality has mainly been a long-term prediction throughout the cycle. However, in a middle of the operation cycle, changes in supplied water quality or unpredictable events may cause the reactor water quality to change rapidly, and may cause a value of the radioactive corrosion product to rise sharply. Prediction on a cycle-by-cycle basis may not be capable of fully coping with such sudden fluctuations.

In the prediction based on the mass balance model in the related art, although the parameters are adjusted based on the actual measurement data, only phenomenon that has been understood can be modeled, so that reproducibility of an actual plant behavior is limited.

Therefore, in a system that controls the reactor water quality, a technique capable of more accurately predicting a behavior of the reactor water quality is desired.

SUMMARY OF THE INVENTION

According to one aspect of the invention, a device for prediction of reactor water quality of a nuclear reactor in a nuclear power plant includes one or more processors, and one or more storage devices. The one or more storage devices are configured to store a reactor water quality prediction model which is learned using learning data and with which future reactor water quality is predicted. An explanatory variable of the reactor water quality prediction model includes a value in a predetermined period unit that is generated from data acquired in an operating nuclear power plant. The one or more processors are configured to generate the value in a predetermined period unit from data acquired in a target operating nuclear power plant, and acquire a predicted value of the reactor water quality in the target nuclear power plant based on the reactor water quality prediction model and the value in a predetermined period unit.

According to an aspect of the invention, more accurate prediction of reactor water quality of a nuclear reactor can be executed.

BRIEF DESCRIPTION OF THE DRAWINGS

FIG. 4 shows a plant information data structure.

FIG. 8B shows explanatory variables of learning data.

DESCRIPTION OF EMBODIMENTS

Figure 1:
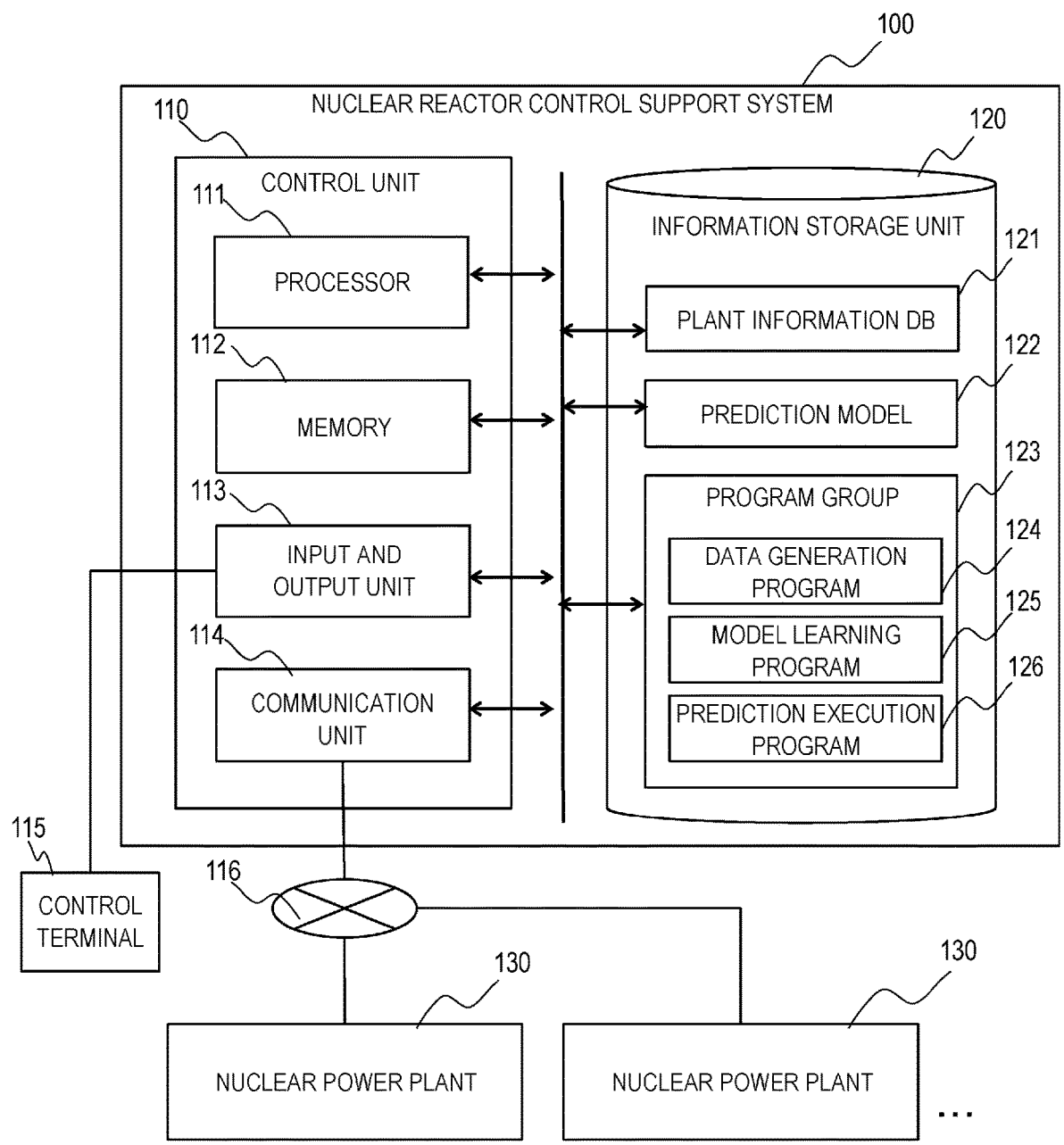
FIG. 1 shows a system configuration.

Hereinafter, embodiments will be described below with reference to the drawings. In the following, a nuclear reactor control support system that controls reactor water quality is disclosed for a purpose of reducing generation of radioactive materials adhering to equipment in a nuclear power plant. The nuclear reactor control support system predicts behaviors of radioactive corrosion products in a reactor, and supports control of the radioactive corrosion products.

Generally, in a nuclear power plant, an operation of the plant is stopped regularly (approximately once for every one to two years) to perform a large-scale inspection. An operation period from a stop period to a stop period is referred to as an "operation cycle".

In the operation of the nuclear power plant, various types of data are measured and collected. In a method disclosed below, these large amounts of data are used to construct a model of a reactor water quality behavior by methods such as machine learning and multiple regression analysis, and reactor water quality is predicted using this model. For example, a concentration of a reactor water radioactive corrosion product (for example, cobalt-60) that is desired to be predicted is used as an objective variable, and various types of operating data of the same day or in the past, water quality measurement data of a water supply system and a reactor water system, and the like are used as explanatory variables, so that relation between the objective variable and the explanatory variables are modeled using the methods such as the machine learning and the multiple regression analysis.

For example, the prediction model can predict a value of the objective variable of a current day from a data set of the explanatory variables of the same day. When it is desired to predict the reactor water quality behavior in the future during a cycle operation, for example, one month from now, the water quality behavior one month ahead can be predicted based on operation information at the present time by learning relation between the objective variable and the explanatory variables by advancing the date of the explanatory variables by one month.

With the above prediction model, the reactor water quality can be predicted during the cycle operation based on latest operation information and water quality information. Accordingly, even when a sudden change in water quality is likely to occur, it is possible to take an early action. Furthermore, using the prediction model, it becomes possible to execute a simulation when an input is changed and study countermeasures, so that rather than relying on experience to optimize water quality, it is possible to propose convincing measures.

Furthermore, since influence of plant operation data and the like, which is not considered in a prediction model in the related art, is also considered in the prediction model derived from various types of plant data, it is possible to provide a prediction result in line with an actual situation. By making predictions more accurate than predictions in the related art, it can be useful for planning periodic inspection work.

Embodiments will be described with reference to FIG. 1 to FIG. 13. FIG. 1 shows a configuration example of a nuclear reactor control support system. The nuclear reactor control support system 100 includes a control unit 110 and an information storage unit 120. The control unit 110 includes a processor 111, a memory 112 (main storage device), an input and output unit 113, and a communication unit 114.

The information storage unit 120 stores a plant information database (DB) 121, a prediction model 122, and a program group 123. The program group 123 includes a data generation program 124, a model learning program 125, and a prediction execution program 126.

The nuclear reactor control support system 100 is connected to a control terminal 115 via the input and output unit 113. The input and output unit 113 may be connected to an input and output device. The nuclear reactor control support system 100 is also connected to one or more nuclear power plants 130 via a network 116. The nuclear power plant 130 includes a measuring instrument and a control unit. The nuclear reactor control support system 100 does not need to be connected to the nuclear power plant 130 online at all times, and may be offline as long as data can be exchanged from the plant 130 as necessary.

The information storage unit 120 includes an auxiliary storage device. The memory 112, the auxiliary storage device or a combination thereof is a storage device, and stores programs and data used by the processor 111. The memory 112 is configured by, for example, a semiconductor memory, and is mainly used for holding a program or data being executed. The processor 111 executes various processes according to the program stored in the memory 112. The processor 111 operates according to the program, so that various functional parts are implemented. The auxiliary storage device is configured by a large-capacity storage device such as a hard disk drive or a solid state drive, and is used for holding a program or data for a long period of time.

The processor 111 can include a single processing unit or a plurality of processing units, and can include a single or a plurality of arithmetic units, or a plurality of processing cores. The processor 111 can be implemented as one or more central processing units, a microprocessor, a microcomputer, a microcontroller, a digital signal processor, a state machine, a logic circuit, a graphics processing device, a chip-on system, and/or any device that handles signals based on a control instruction.

The programs and data that are stored in the auxiliary storage device are loaded into the memory 112 at startup or when needed, and the processor 111 executes the programs, so that various processes of the nuclear reactor control support system 100 are executed. Therefore, in the following, a process executed by the nuclear reactor control support system 100 is a process executed by the processor 111 or the program.

The functions of the nuclear reactor control support system 100 can be implemented in a computer system that includes one or more computers. The one or more computers include one or more processors and one or more storage devices including a non-transient storage medium. The plurality of computers communicate via a network. For example, a part of a plurality of functions of the nuclear reactor control support system 100 may be implemented in one computer, and the other part of the functions may be implemented in the other computers.

Figure 2:
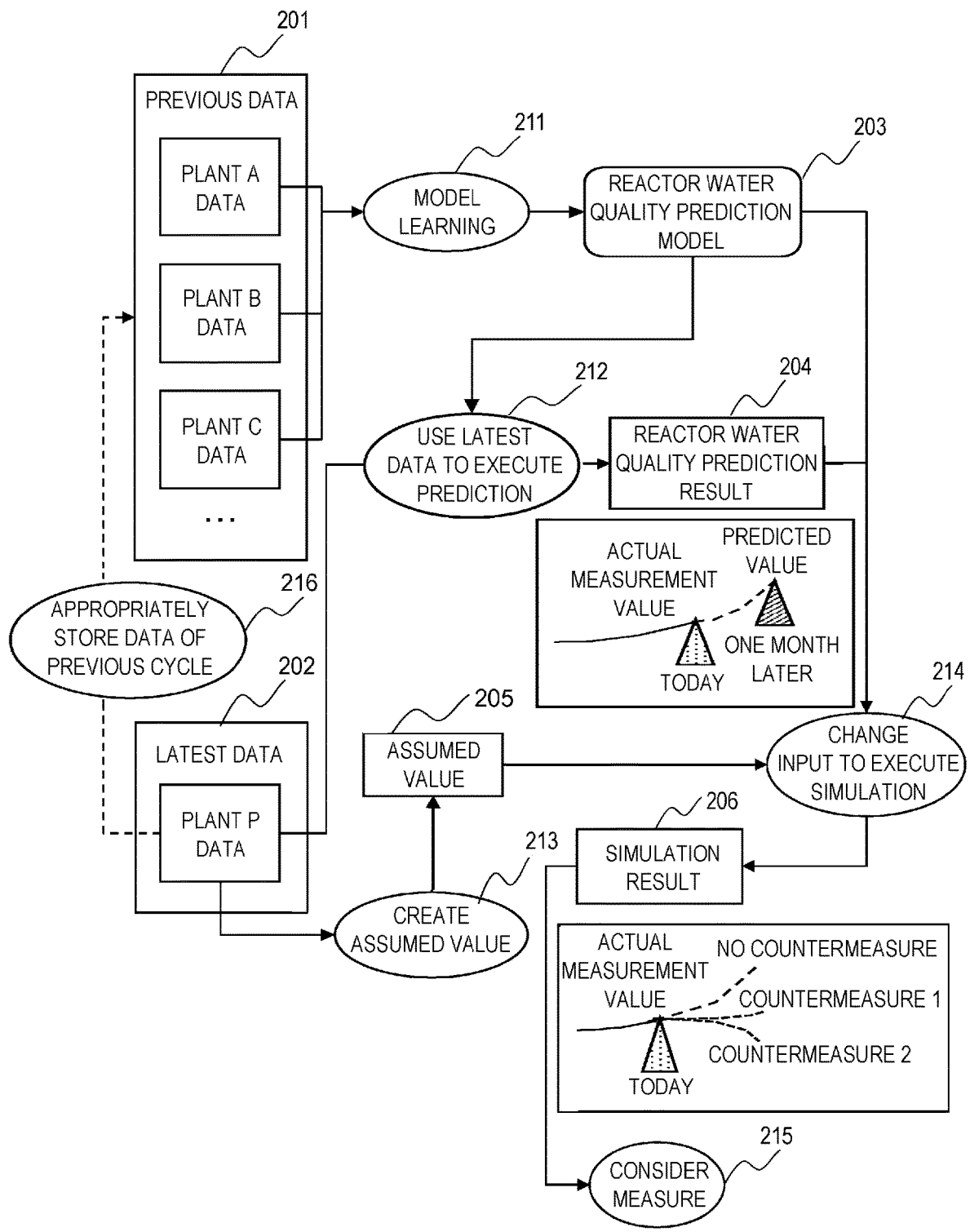
FIG. 2 shows a process flow.

FIG. 2 shows an overall process flow in the nuclear reactor control support system 100. The example shown in FIG. 2 shows a process flow of using previous data 201 (a plant A, a plant B, and a plant C) for model learning, and predicting a behavior of reactor water quality (here, an example of cobalt-60 is described) using latest data 202 of a plant P.

Using the previous data of different plants as a learning model, reactor water quality of a target plant can be predicted even when data of the target plant is insufficient. A highly versatile prediction model can be generated by learning the previous data of a plurality of different plants. Here, the data 201 in a previous cycle of each plant is stored in the plant information DB 121 in FIG. 1.

In a situation where the previous data 201 in at least one plant is accumulated, the nuclear reactor control support system 100 generates a reactor water quality prediction model 203 by a model learning process 211 to be described later and stores the reactor water quality prediction model 203 in a predetermined place. On the other hand, at a timing when the latest data 202 is obtained at the plant P, the nuclear reactor control support system 100 predicts future reactor water quality based on the reactor water quality prediction model 203 and the latest data (212).

Based on a prediction result 204, a user can determine a future trend of reactor water radioactivity during a cycle application, use the trend as an input to estimate a working dose during a periodic inspection, and take countermeasures such as making an inspection plan. The nuclear reactor control support system 100 generates an assumed value 205 when some countermeasures are taken (213) and gives the assumed value 205 to the same prediction model 203. Accordingly, the nuclear reactor control support system 100 can execute simulations for a plurality of countermeasures (214). The user can consider future measures by comparing the countermeasures (215).

Here, the data of the plant P treated as the latest data 202 can be stored in the plant information DB 121 as the previous data 201 when a cycle is completed (216). The nuclear reactor control support system 100 may execute the model learning 211 at a timing when the previous data 201 is added, and may update the reactor water quality prediction model 203. Accordingly, the more appropriate reactor water quality prediction model 203 can be obtained for the target plant.

Figure 3:
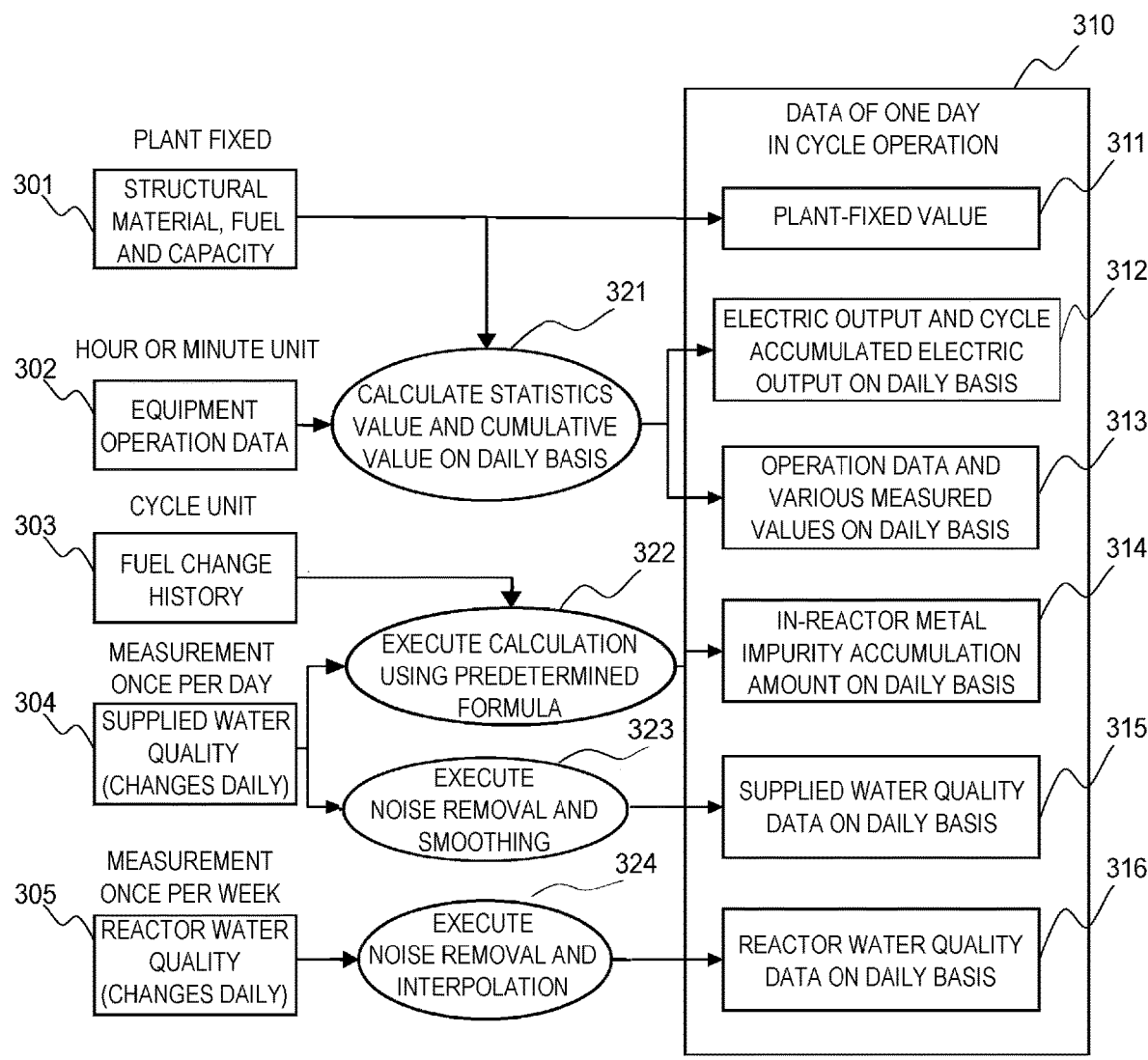
FIG. 3 shows a data structure and a main generation procedure.

Next, generation of the data stored in the plant information DB 121 in FIG. 1 will be described with reference to FIGS. 3 to 6. FIG. 3 shows an outline of the data and a main generation procedure. Data available for the model learning includes, for example, plant-fixed data 301 that shows components constituting the plant such as a type of structural materials and fuel bodies and a capacity, equipment operation data 302 that is collected every moment, a fuel change history 303 held on a cycle-by-cycle basis, data (measured value) 304 on supplied water quality measured approximately once a day, and data (measured value) 305 on reactor water quality measured approximately once a week.

When the reactor water quality prediction model 203 is created using methods such as machine learning, it is important to make data granularity (period unit) uniform. Accordingly, an appropriate prediction can be executed. In the example in FIG. 3, it is assumed that a data set (daily data) 310 for a certain day during the cycle operation is created. Here, a period unit of the data may not be on a daily basis, and the data set may be a weekly or monthly data set, or a half-day unit or time zone unit data set. However, when a time interval is too fine, a capacity for storing the data may become large, and when the time interval is too coarse, the number of pieces of data used for the model learning may become small.

Here, the daily data set 310 is created. The data generation program 124 sets a plant-fixed value such as a plant configuration value as it is as a plant-fixed value 311. The data generation program 124 calculates a statistics value and a cumulative value such as a daily average value and a daily maximum value based on a combination of the plant-fixed data 301 and the equipment operation data 302 (321). Accordingly, the data generation program 124 generates a daily electric output and in-cycle cumulative electric output 312, and daily operation data and various measured values 313.

The data generation program 124 calculates a daily in-reactor metal impurity accumulation amount 314 based on the fuel change history 303 held on a cycle-by-cycle basis and the daily supplied water quality measured value 304 using a predetermined formula to be described later with reference to FIG. 6 (322). The data generation program 124 basically uses the supplied water quality measured value 304 as it is as daily supplied water quality data 315. The data generation program 124 executes a process such as noise removal and smoothing as necessary (323). For example, the data generation program 124 executes the noise removal and interpolation process on the reactor water quality 305 measured on a weekly basis (324), and uses the processed reactor water quality 305 as daily reactor water quality data 316.

FIG. 4 shows a configuration example of the data stored in the plant information DB 121. The daily data 310 generated by the procedure described with reference to FIG. 3 corresponds to one row in a table shown in FIG. 4. The data is daily stored for each plant. The plant information DB 121 includes labels for a plant name 331, a date 332, and a cycle number 333, and types of data (the plant-fixed value 311, the electric output 312, the operation data and measured values 313, the in-reactor metal impurity accumulation amount 314, supplied water quality 315, and reactor water quality 316) described with reference to FIG. 3.

Figure 5:
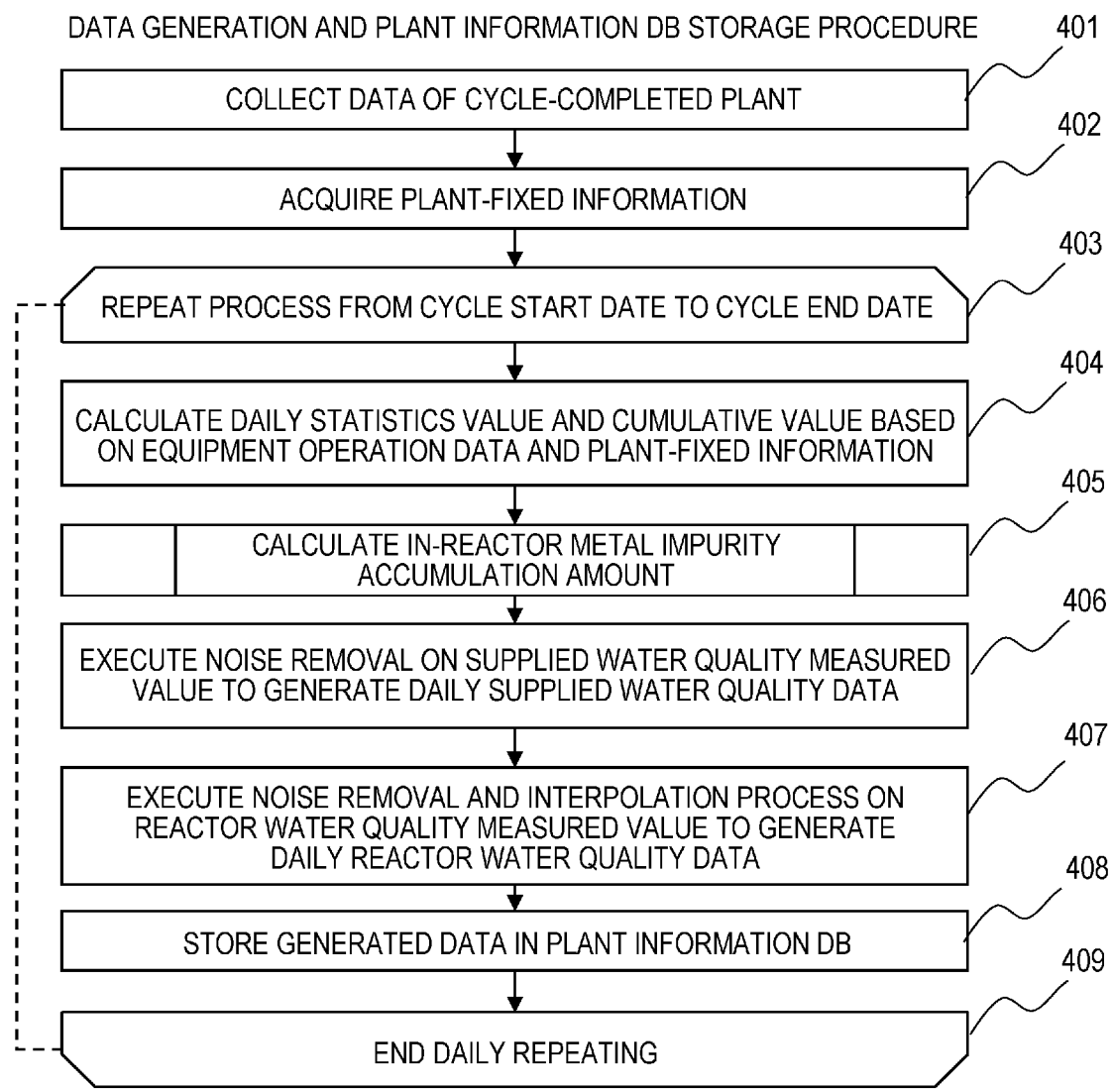
FIG. 5 shows a data generation and plant information DB storage procedure.

FIG. 5 shows a flow chart of the generation procedure shown in FIG. 3. Firstly, the data generation program 124 collects data of a cycle-completed plant online or offline (using a storage medium) (401). The data generation program 124 acquires plant-fixed information (402), and then repeats the following processes executed on the acquired data in a cycle for each day from a cycle start date to a cycle end date (403).

The data generation program 124 calculates a daily statistics value and a cumulative value based on the equipment operation data and the plant-fixed information (404). The data generation program 124 calculates an in-reactor metal impurity accumulation amount based on the fuel change history held on a cycle-by-cycle basis and the supplied water quality using the method to be described later with reference to FIG. 6 (405). The data generation program 124 executes noise removal on the supplied water quality measured value to generate daily supplied water quality data (406), and then executes noise removal and interpolation process on the reactor water quality measured value to generate daily reactor water quality data (407). The data generation program 124 stores the generated data in the plant information DB 121 (408).

As described in the description with reference to FIG. 3, the repeated process in step 403 does not necessarily have to be a daily process, and may be a process at another time interval such as a weekly process or a half day process.

Next, a method of calculating the in-reactor metal impurity accumulation amount will be described with reference to FIG. 6. Metal impurities brought in from a water supply system to the reactor are removed by a nuclear reactor purification system, or adhere to a surface of a fuel body and structures in the reactor. The attached metal impurities are activated by neutron irradiation on the surface of the fuel body, and become the radioactive corrosion products.

Therefore, it can be said that the in-reactor metal impurity accumulation amount is greatly involved in generation of the radioactive corrosion products in the reactor. Among the metal impurities adhering to the structures in the reactor, metal impurities adhering to the surface of the fuel body are taken out of the reactor when being replaced with a new fuel body as a spent fuel body. Therefore, the in-reactor metal impurity accumulation amount is calculated by (amount brought in from the water supply system)−(adhering amount of spent fuel).

Figure 6:
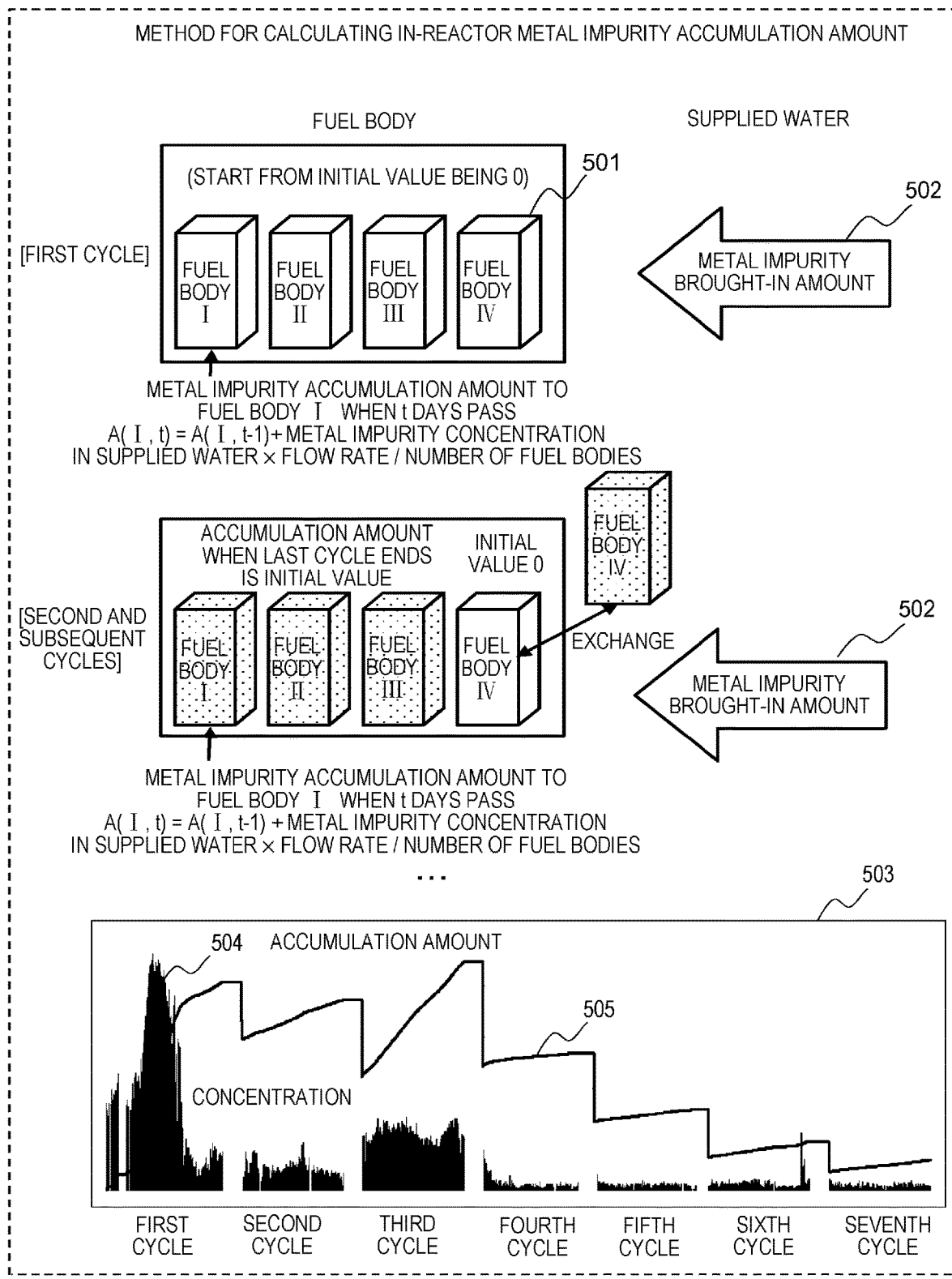
FIG. 6 shows a metal impurity accumulation amount calculation method.

As shown in FIG. 6, it is assumed that all metal impurities 502 brought in from the water supply system in a first cycle (initial cycle) adhere to a fuel body 501. An initial value of a metal impurity accumulation amount in the fuel body 501 in the first cycle is 0. During a first regular inspection after the first cycle is completed, some spent fuel bodies are taken out of the reactor and the same number of new fuel bodies are loaded.

An in-reactor accumulation amount at a start of a second cycle is a value obtained by subtracting an amount adhering to the spent fuel body that is taken out of the reactor from a metal impurity brought-in amount in the first cycle. An in-reactor accumulation amount at an end of the second cycle is a value obtained by adding a metal impurity brought-in amount in the second cycle to the value at the start of the second cycle.

An in-reactor accumulation amount at a start of a third cycle is a value obtained, similarly to the second cycle, by subtracting an amount adhering to the spent fuel body that is replaced in a second regular inspection from the in-reactor accumulation amount at the end of the second cycle. The same calculation can be executed in the third and subsequent cycles to calculate an in-reactor accumulation amount in each cycle.

When it is assumed that the number of the fuel bodies is 4, a concentration of metal impurity brought in from the water supply system on a t day is R (t), and a water supply flow rate on the t day is F (t).

An in-reactor metal impurity accumulation amount A (n, t) adhering to a fuel body n after t days are passed from a start of a cycle is expressed by the following formula.

$$A(n,t)=A(n,t-1)+R(t)*F(t)/4 \quad \text{(Equation 1)}$$

An in-reactor metal impurity accumulation amount A (t) after t days are passed from the start of the cycle is expressed by the following formula.

$$A(t)=\Sigma_{n=1}^{4}A(n,t) \quad \text{(Equation 2)}$$

Here, an initial value of the in-reactor metal impurity accumulation amount A (n, t) adhering to the fuel body n at the start of the cycle is zero for all n in the first cycle, and is an accumulation amount at an end of a previous cycle in the second and subsequent cycles. However, by referring to the fuel change history, when a corresponding fuel body is replaced, the initial value is reset to zero. In this way, as shown in a graph 503, an in-reactor metal impurity accumulation amount 505 with respect to a daily metal impurity concentration 504 is calculated in each cycle.

Figures 7, 8A:
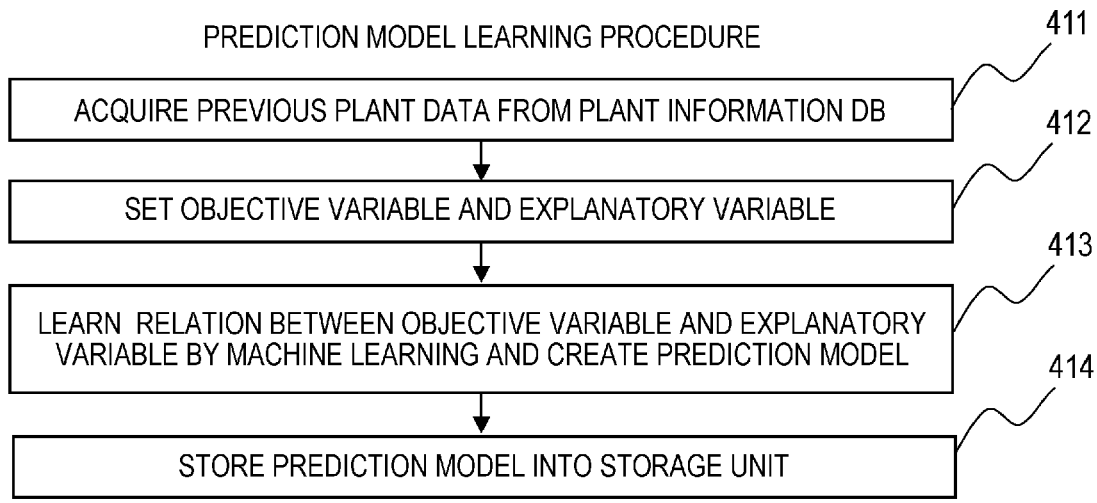
FIG. 7 shows a prediction model learning procedure.
FIG. 8A shows objective variables of learning data.

Next, prediction model learning will be described with reference to FIGS. 7 to 10. FIG. 7 shows a prediction model learning procedure. The model learning program 125 acquires previous plant data used for learning from the plant information DB 121 (411). The model learning program 125 sets an objective variable and an explanatory variable (412), and then uses existing methods such as the machine learning and the multiple regression analysis to model relation between the objective variable and the explanatory variable (413). The model learning program 125 stores the created prediction model 122 in the information storage unit 120 (414).

Here, structural examples of the learning data are shown in FIGS. 8A and 8B for the objective variable and the explanatory variable that are set in step 412. FIG. 8A shows an objective variable table 507 and FIG. 8B shows an explanatory variable table 508. In the objective variable table 507, items 571, 572, 573 respectively correspond to the items 331, 332, 333 having the same names in the plant information 121 shown in FIG. 4. An item 574 indicates the objective variable (predicted variable). In the explanatory variable table 508, items 581 to 588 respectively correspond to the items 331, 332, 333, 311 to 315 having the same names in the plant information 121 shown in FIG. 4.

In the examples shown in FIGS. 8A and 8B, a concentration of cobalt-60 in the reactor water after 30 days from a certain date (572, 582) is set to the objective variable (574), and various types of data (584 to 588) of a current date are set to the corresponding explanatory variables. The explanatory variables include a plant fixed value 584. Accordingly, using prediction models obtained by learning the learning data from different plants, reactor water quality of a target plant can be more appropriately predicted. In this example, the reactor water quality is not included in the explanatory variables. The combination of the objective variable and the explanatory variable is not limited to this, and some patterns can be considered depending on an actual application. The patterns are shown in FIGS. 9A, 9B, 10A and 10B.

Figure 9A:
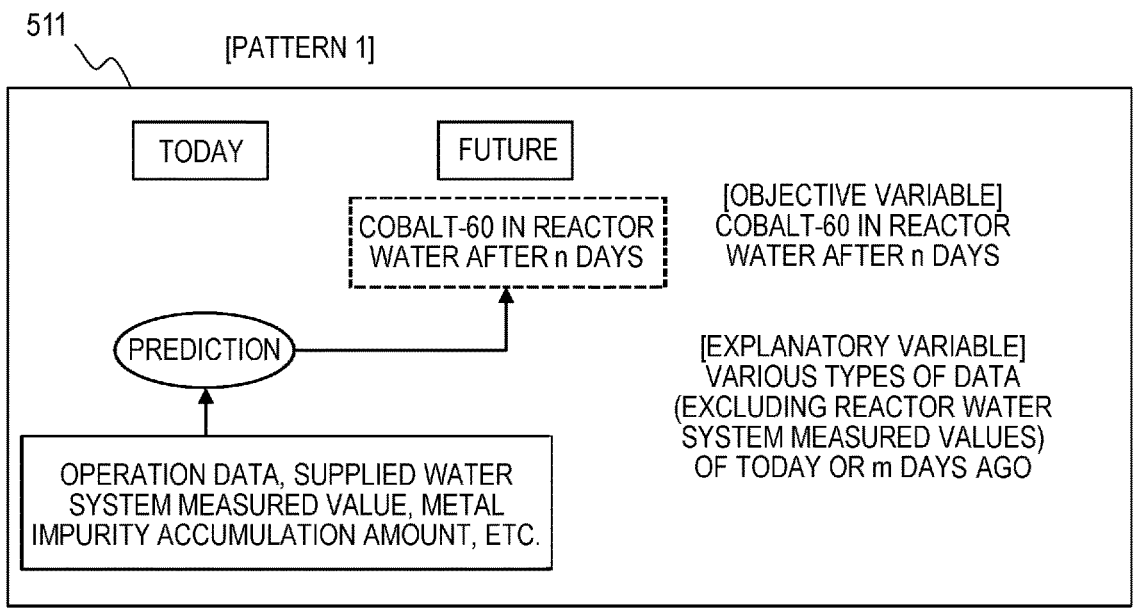
FIG. 9A shows a pattern example of the objective variable and the explanatory variable.

The examples in FIGS. 8A and 8B correspond to a combination of the objective variable and the explanatory variable of a pattern 1 (511) in FIG. 9A. The pattern 1 is a pattern in which various types of data (excluding measured values of the reactor water system) of the current date are used as the explanatory variables to predict the concentration of cobalt-60 in the reactor water n days later (n is a natural number). Instead of the various types of data of the current date, various types of data (excluding the measured values of the reactor water system) m days ago may be used as the explanatory variables. Here, m is a predetermined natural number. A reason for excluding the reactor water system data from the explanatory variables is that, in general, the measured values of the reactor water system are often acquired later than other data, and it is generally difficult to acquire the value of the current date during the cycle application.

Figure 9B:
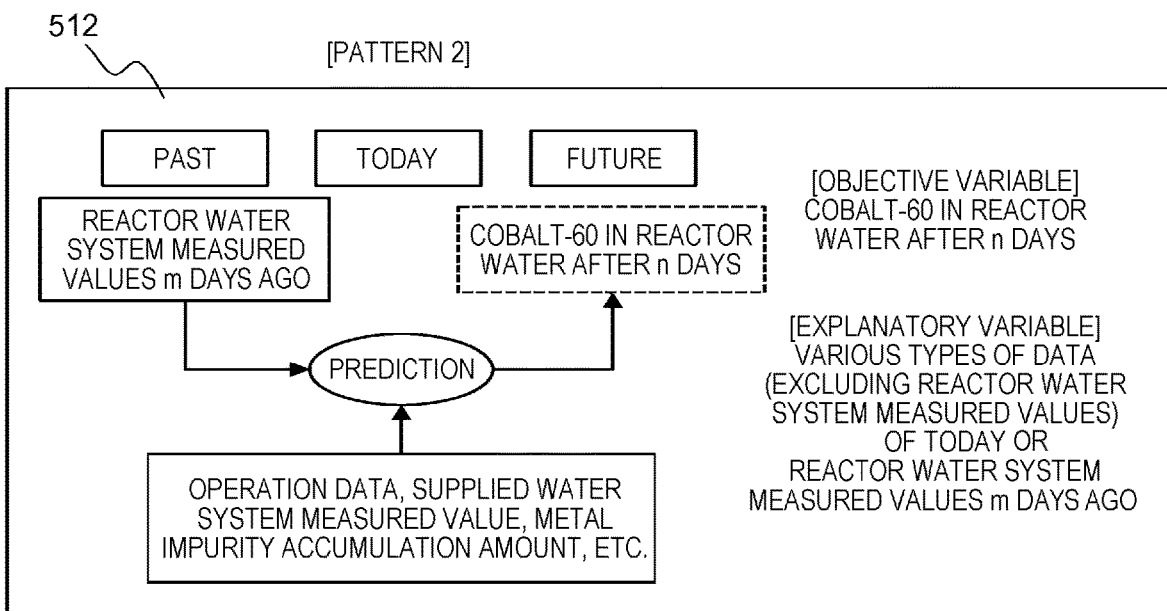
FIG. 9B shows a pattern example of the objective variable and the explanatory variable.

FIG. 9B shows a pattern 2 (512) which is another pattern example of the combination of the objective variable and the explanatory variable. The pattern 2 (512) puts the data of the reactor water system in the explanatory variables on a premise that the measured values of the reactor water system can be acquired with a delay. The pattern 2 (512) predicts the cobalt-60 concentration in the reactor water n days later by using a value of only the data of the reactor water system m days ago and combining the value with other data of the current date. Accordingly, the reactor water quality can be predicted more appropriately in a plant in which the measured value of the reactor water system is acquired later than the measured value of the water supply system. A date of each explanatory variable may be set individually.

Figure 10A:
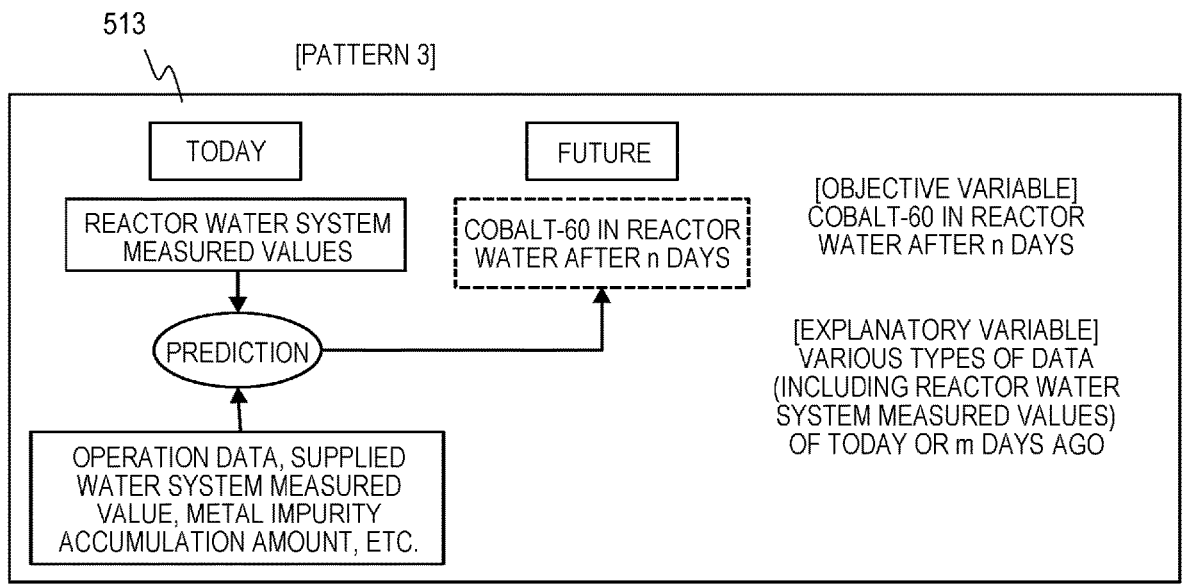
FIG. 10A shows a pattern example of the objective variable and the explanatory variable.

FIG. 10A shows a pattern 3 (513) which is another pattern example of the combination of the objective variable and the explanatory variable. By assuming that the measured value of the reactor water system and other data are available on the same day, the pattern 3 (513) uses both pieces of data to predict the cobalt-60 concentration in reactor water n days later. When there is data for which actual measurement values cannot be obtained on the current date, a value of the data may be an estimated value as described with reference to FIG. 3. For example, the value of the reactor water quality of the current date measured on a weekly basis can be obtained by executing the interpolation process on the previous measured values.

Figure 10B:
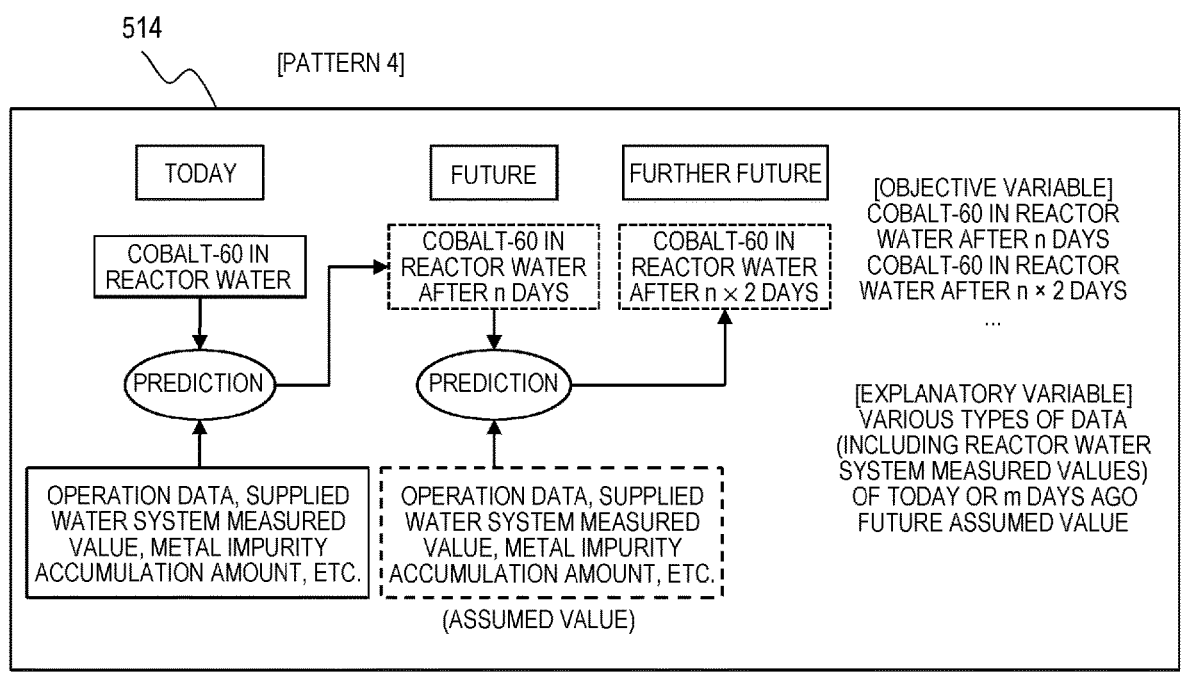
FIG. 10B shows a pattern example of the objective variable and the explanatory variable.

FIG. 10B shows a pattern 4 (514) which is another pattern example of the combination of the objective variable and the explanatory variable. The pattern 4 (514) is an application of the Pattern 3 (513). The pattern 4 (514) predicts the cobalt-60 concentration in the reactor water n days later using the explanatory variables of the current date or m days ago, and then uses this value to predict the cobalt-60 concentration in the reactor water in the future (n×2 days later).

At this time, the simulation can be executed by inputting the assumed value (estimated value) of a day after n days or of a day that is m days before the day after n days into each of the explanatory variables. As the assumed value, it is possible to use a value assuming that a current value is remained the same and a value when countermeasures such as intervention in supplied water quality by injecting iron into supplied water and equipment control are taken. By giving the assumed value under a plurality of conditions as explanatory variables to execute simulations, and comparing the simulations, future measures can be considered.

Figure 11:
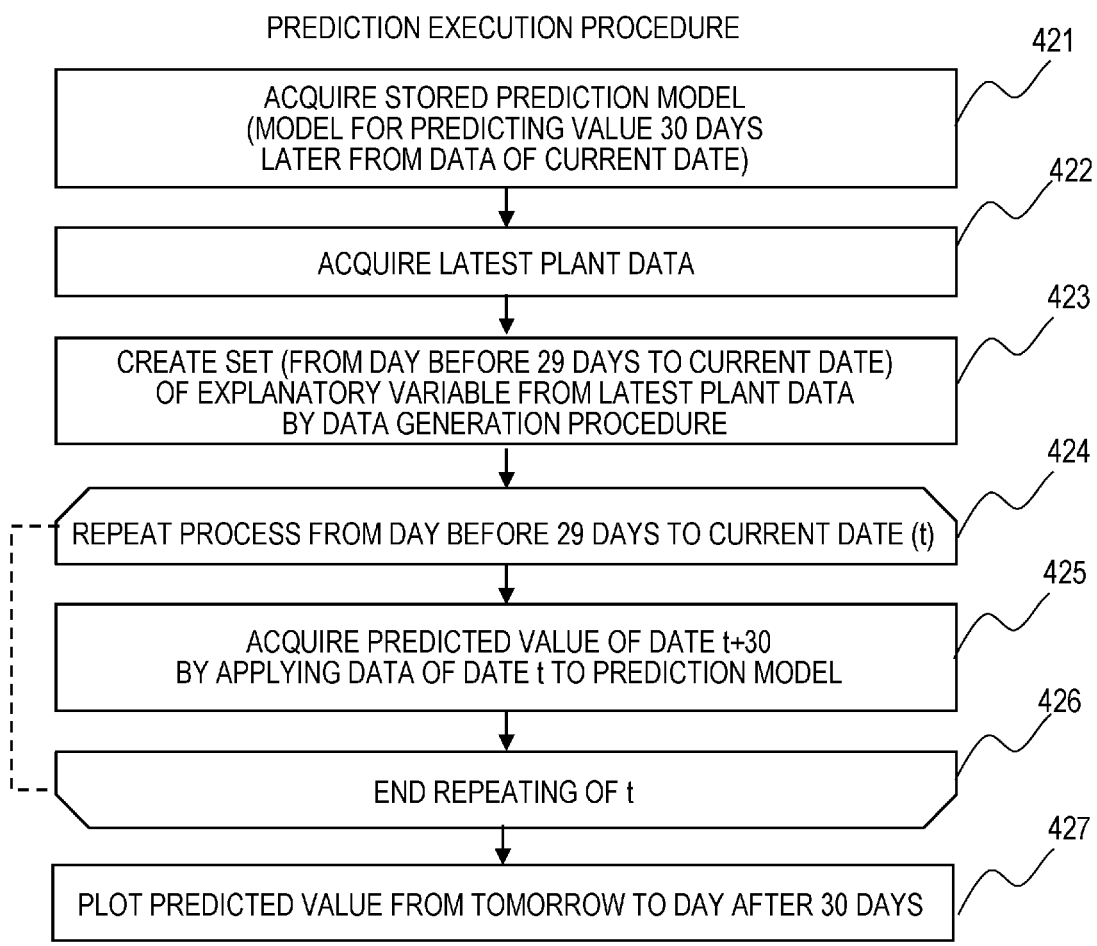
FIG. 11 shows a prediction execution procedure.

FIG. 11 shows a prediction execution procedure. Here, it is assumed that the model 122 is generated using the pattern 1 or the pattern 3 among the patterns shown in FIGS. 9A to 10B. The model 122 predicts the objective variable 30 days later from the explanatory variable of the current date. Firstly, the prediction execution program 126 acquires the stored prediction model 122 from the information storage unit 120 (421), and then acquires the latest plant data (422).

The prediction execution program 126 generates a set of explanatory variables from 29 days ago to the current date from this latest data by the above-mentioned data generation procedure (423). Processes are repeated, for example, explanatory variables 29 days ago are applied to the prediction model 122 to execute prediction one day later, and explanatory variables 28 days ago are applied to the prediction model 122 to execute prediction two days later (424 to 426). Accordingly, a predicted value after 1 day to 30 days from today can be obtained. The prediction execution program 126 plots the obtained results and displays the results on a screen (427).

Figure 12:
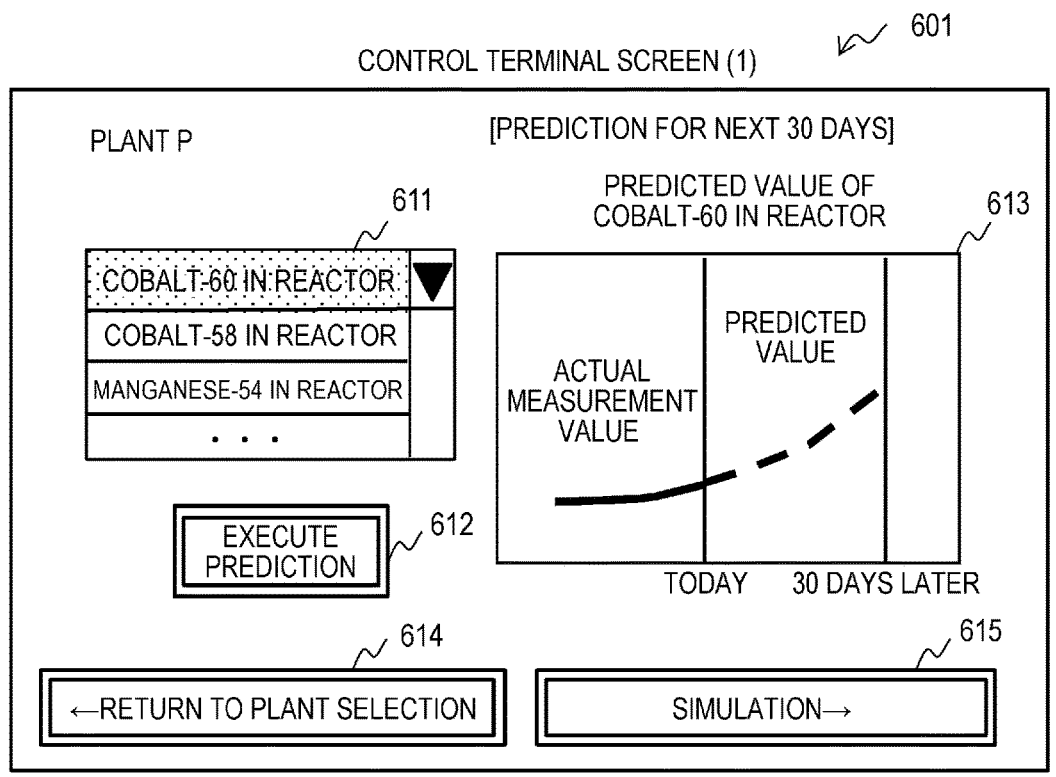
FIG. 12 shows a control terminal screen (1).

FIG. 12 shows an example of the screen 601 plotted in step 427 in the prediction execution procedure shown in FIG. 11. The screen 601 is displayed on a display device (output device) of the control terminal 115. On the screen 601, results of predicting the cobalt-60 concentration in the reactor in the plant P are plotted in a graph 613. The cobalt-60 is a main component of radioactive corrosion products. On the screen 601, values up to today are plotted as actual measurement values, and values of a next day and after the next day are plotted as predicted values in time series.

The user can select a prediction target by a selection box 611 on the screen 601. Prediction targets other than the cobalt-60 can also be selected, and prediction models each corresponding to a respective one of the prediction targets have been generated. When a prediction execution button 612 is selected, the graph 613 of a result of predicting the cobalt-60 concentration in the reactor is displayed. When a button 614 is selected, the user can return to a plant selection screen. By selecting a button 615, a screen for simulation can be displayed.

Figure 13:
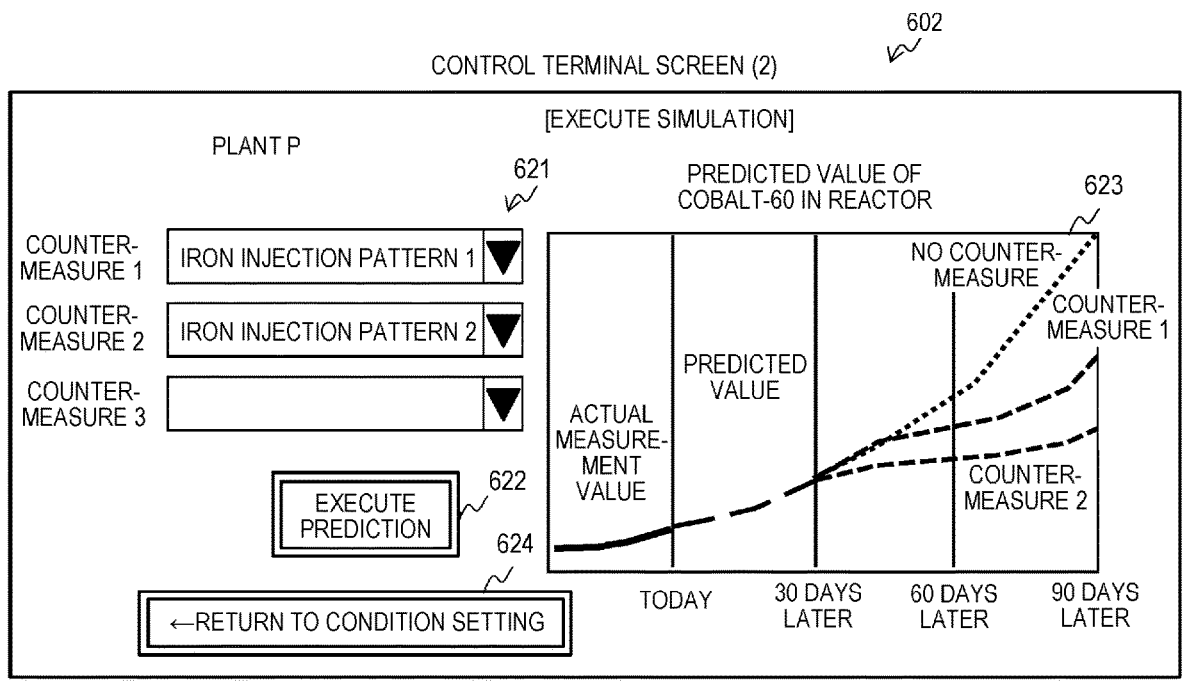
FIG. 13 shows a control terminal screen (2).

FIG. 13 shows another screen example 602 displayed on the screen of the control terminal 115. The screen 602 proceeds one step further from the prediction and shows a simulation execution result. As shown in the pattern 4 (514) in FIG. 10B, the prediction execution program 126 inputs an assumed value into the explanatory variable and executes the prediction further after 30 days.

The screen 602 displays, depending on the selection of the button 622, a simulation result 623 including the prediction according to a countermeasure in addition to a prediction result of an "unmeasured" situation assuming that a current value continues. The user can specify a countermeasure to be simulated in a countermeasure selection box 621.

The user inputs an assumed value for each of the countermeasures on another screen (not shown) displayed by pressing a button 624. The prediction execution program 126 obtains the prediction result according to the countermeasure by inputting the assumed value when the specified countermeasure is implemented into the prediction model 122. As shown in FIG. 13, by executing simulations under a plurality of conditions and comparing the simulations, future measures can be considered.

The invention is not limited to the embodiments described above, and includes various modifications. For example, the embodiments described above are described in detail for easy understanding of the invention, and the invention is not necessarily limited to those including all the configurations described above. A part of the configuration according to one embodiment can be replaced with the configuration according to another embodiment, and the configuration according to one embodiment can be added to the configuration according to another embodiment. It is possible to add, delete, and replace other configurations for a part of the configuration according to each embodiment.

Each of the above-described configurations, functions, process units, and the like may be partially or entirely implemented by hardware by, for example, executing design using an integrated circuit. The above-mentioned configurations, functions, and the like may be implemented by software by means of a processor interpreting and executing a program for implementing each function. Information of programs, tables, files or the like for implementing each function can be placed in a recording device such as a memory, a hard disk, and a solid state drive (SSD), or a recording medium such as an IC card and an SD card. Among control lines and information lines, those considered to be necessary for the description are shown, and not all the control lines and the information lines are necessarily shown on the product. In practice, it may be considered that almost all the configurations are connected to one another.

What is claimed is:

1. A device for prediction of reactor water quality of a nuclear reactor in a nuclear power plant, the device comprising:
one or more processors;
a display device; and
one or more storage devices, wherein
the one or more storage devices store a reactor water quality prediction model which is learned using learning data and with which future reactor water quality is predicted,
an explanatory variable of the reactor water quality prediction model includes a value in a predetermined period unit that is generated from data acquired in an operating nuclear power plant;
the one or more processors are configured to:
generate the value in a predetermined period unit from data acquired in a target nuclear power plant by calculating, as at least a part of the explanatory variable, a daily metal impurity accumulation amount in the nuclear reactor in the target nuclear power plant based on:
a fuel change history held on a cycle-by-cycle basis; and
a daily supplied water quality measured value;
acquire a first predicted value of the reactor water quality in the target nuclear power plant based on:
the reactor water quality prediction model; and
the value in a predetermined period unit;
receive information of a plurality of countermeasures for improving the reactor water quality; and
upon receiving the information of the plurality of countermeasures:
acquire other predicted values of the reactor water quality in the target nuclear power plant based on the countermeasures by inputting assumed values for the countermeasures, respectively and
simultaneously display, on the display device:
the first predicted value which is not based on a countermeasures; and
the other predicted values which are based on the countermeasures, respectively,
to enable comparison to determine an appropriate countermeasure from the plurality of countermeasures.

2. The device according to claim 1, wherein
the data acquired in the target nuclear power plant includes values in different period units, and
the one or more processors are configured to generate the value in a predetermined period unit from each of the values in different period units.

3. The device according to claim 1, wherein
the explanatory variable of the reactor water quality prediction model includes a fixed value of a component constituting the nuclear power plant.

4. The device according to claim 1, wherein
the value in a predetermined period unit is a value within an operation cycle of the target nuclear power plant, and
the one or more processors are configured to acquire a predicted value of the reactor water quality in the target nuclear power plant in the future within the operation cycle from the reactor water quality prediction model.

5. The device according to claim 1, wherein
the learning data includes previous data of a nuclear power plant different from the target nuclear power plant.

6. The device according to claim 1, wherein
the one or more processors are configured to execute learning of the reactor water quality prediction model with the data acquired in the target nuclear power plant serving as learning data.

7. The device according to claim 1, wherein
the explanatory variable of the reactor water quality prediction model includes a water supply system measured value and a reactor water system measured value older than the water supply system measured value.

8. The device according to claim 1, wherein
the reactor water quality prediction model predicts a future value of a variable included in the explanatory variable of the reactor water quality prediction model,
the explanatory variable includes a changing value in the target nuclear power plant, and
the one or more processors are configured to acquire a future second predicted value from a first predicted value of the reactor water quality prediction model based on the reactor water quality prediction model, the first prediction value, and an assumed value of the changing value.

9. The device according to claim 1, wherein
the one or more processors are configured to output the predicted value of the reactor water quality in the target nuclear power plant to an output device.

10. A method for prediction of reactor water quality of a nuclear reactor in a nuclear power plant by a device, wherein
the device comprises one or more processors,
the device stores a reactor water quality prediction model which is learned using learning data and with which future reactor water quality is predicted, and
an explanatory variable of the reactor water quality prediction model includes a value in a predetermined period unit that is generated from data acquired in an operating nuclear power plant,
the method comprising the steps of:
generating, by the device, the value in a predetermined period unit from data acquired in a target nuclear power plant by calculating, as at least a part of the explanatory variable, a daily metal impurity accumulation amount in the nuclear reactor in the target nuclear power plant based on:
a fuel change history held on a cycle-by-cycle basis; and
a daily supplied water quality measured value;
acquiring, by the device, a first predicted value of the reactor water quality in the target nuclear power plant based on:
the reactor water quality prediction model; and
the value in a predetermined period unit;
receiving, by the device, information of a plurality of countermeasures for improving the reactor water quality; and
upon receiving the information of the plurality of countermeasures:
acquiring other predicted values of the reactor water quality in the target nuclear power plant based on the countermeasures by inputting assumed values for the countermeasures, respectively; and
simultaneously displaying on a display device:
the first predicted value which is not based on a countermeasure; and
the other predicted values which are based on the countermeasures, respectively,
to enable comparison to determine an appropriate countermeasure from the plurality of countermeasures.

* * * * *